US00PP28719P3

(12) United States Plant Patent
Bédard

(10) Patent No.: US PP28,719 P3
(45) Date of Patent: Dec. 5, 2017

(54) HYBRID TEA ROSE PLANT NAMED 'WEKDADODA'

(50) Latin Name: *Rosa hybrida*
Varietal Denomination: WEKdadoda

(71) Applicant: Early Morning LLC, Lawrenceburg, IN (US)

(72) Inventor: Christian Bédard, Placentia, CA (US)

(73) Assignee: Early Morning LLC, Lawrenceburg, IN (US)

( * ) Notice: Subject to any disclaimer, the term of this patent is extended or adjusted under 35 U.S.C. 154(b) by 0 days.

(21) Appl. No.: 14/757,133

(22) Filed: Nov. 23, 2015

(65) Prior Publication Data

US 2017/0150663 P1 May 25, 2017

(51) Int. Cl.
*A01H 5/02* (2006.01)

(52) U.S. Cl.
USPC ..... Plt./130

(58) Field of Classification Search
USPC ..... Plt./130, 138, 102, 107, 141, 149
CPC ..... A01H 5/0222; A01H 5/0216; A01H 5/02; A01H 5/00
See application file for complete search history.

(56) References Cited

U.S. PATENT DOCUMENTS

PP23,476 P2 3/2013 Carruth

OTHER PUBLICATIONS

Brecks Downton Roses—Pretty Lady Rose Dowton Abbey Hybrid Tea Rose 2016, retrieved on Mar. 9, 2017, retrieved from the Internet at <https://www.brecks.com/product/New_for_2016_Downton_Abbey_Rose_> 3 pp.*

Weeks Roses Pretty Lady Rose 2015, retrieved on Mar. 9, 2017, retrieved from the Internet at <http://www.weeksroses.com/_Roses/PrettyLadyRose.html> 2 pp.*

* cited by examiner

*Primary Examiner* — June Hwu
(74) *Attorney, Agent, or Firm* — McKee, Voorhees & Sease, PLC

(57) ABSTRACT

A new variety of Hybrid Tea rose suitable for garden decoration, having flowers of deep pink coloration.

1 Drawing Sheet

Classification: The present invention relates to a new *Rosa hybrida* plant.

Variety denomination: The new plant has the varietal denomination 'WEKdadoda'.

BACKGROUND OF THE INVENTION

This invention relates to a new and distinct variety of Hybrid Tea Rose. It has as its seed parent the variety known as 'WEKmerewby' (U.S. Plant Pat. No. 23,476) and as its pollen parent the variety known as 'WEKmajuchi' (U.S. Plant Pat. No. 26,793).

SUMMARY OF THE INVENTION

Among the features which distinguish the new variety from other presently available and commercial rose cultivars known to the inventor are the following combinations of characteristics: its high degree of resistance to powdery mildew, downy mildew and rust, its excellent color stability throughout the life of the flower and its moderately strong damask to peony-like with hints of spices fragrance. The plant has an upright somewhat spreading growing habit, suitable for outdoor garden decoration.

Asexual reproduction of the new variety by T-budding as performed in Kern County and Pomona, Calif., shows that the foregoing and other distinguishing characteristics come true to form and are established and transmitted through succeeding asexual propagations. 'WEKdadoda' may be asexually propagated by cuttings, budding and grafting. The budding and grafting successfully occurred on the plant/rootstock *Rosa hybrida* 'Dr. Huey' (not patented).

COMPARISON WITH PARENTS

The new rose may be distinguished from its seed parent, 'WEKmerewby' by the following combination of characteristics: whereas 'WEKdadoda' bears very double flowers (about 30 to 55 petals), 'WEKmerewby' bears double flowers with significantly lesser petalage (about 26 to 38 petals). The new variety has an upright somewhat spreading medium height to somewhat tall growing habit (about 145 to about 180 cm. in height), whereas the seed parent has an upright taller growing habit (about 170 to about 190 cm. in height).

The new variety may be distinguished from its pollen parent, 'WEKmajuchi' by the following combination of characteristics: whereas 'WEKdadoda' bears very double flowers (about 30 to 55 petals) of deep pink coloration, 'WEKmajuchi' bears double flowers of pure even gold yellow coloration with lesser petalage (about 26 to 42 petals). The new variety is classified as a Hybrid Tea rose with an upright somewhat spreading medium height to somewhat tall growing habit (about 145 to about 180 cm. in height), whereas the pollen parent is classified as a Floribunda rose with a bushy upright significantly shorter growing habit (about 120 to about 160 cm. in height).

COMPARISON WITH THE CLOSEST COMMERCIALLY AVAILABLE CULTIVAR

The closest commercially available cultivar to the new variety is the seed parent 'WEKmerewby' (U.S. Plant Pat. No. 23,476).

BRIEF DESCRIPTION OF ILLUSTRATION

The accompanying photograph illustrates the new variety and shows the flowering thereof from bud to full bloom depicted in color as nearly correct as it is possible to make in a color illustration of the character. The branches used for the photograph came from 3 to 4 year-old rose plants of the new variety grown outdoors in Pomona, Calif. in the month of November. Throughout this specification, color references and/or values are based upon The Colour Chart of The Royal Horticultural Society (1966) except where common terms of color definition are employed.

DESCRIPTION OF THE NEW VARIETY

The following description is of 3 to 4 year-old rose plants of the new variety grown outdoors in Pomona, Calif. in the month of November. Phenotypic expression may vary with environmental, cultural and climatic conditions, as well as differences in conditions of light and soil.

FLOWER

The new variety usually bears its flowers singly, sometimes in clusters of two to four or more per stem. Flowers may be borne in regular rounded clusters on medium to somewhat long stems (about 23 to about 105 cm.). The cluster ranges from about 17.3 to about 20.5 cm. in diameter. Outdoors, the plant blooms abundantly and nearly continuously during the growing season. The flowers have a moderately strong damask to peony-like with hints of spices fragrance.

BUD

The peduncle is about 2.7 to about 6.1 cm. in length, of average to somewhat heavy caliper (about 0.3 to about 0.5 cm. in diameter), and usually erect. It is smooth, with very few stipitate glands and hairs. Peduncle color is between 146C and 144A sometimes moderately suffused, especially on the side exposed to the sun, with between 183B and 187B.

Before the calyx breaks, the bud is about 1.2 to about 1.8 cm. in diameter at the widest point, about 1.5 to about 2.7 cm. in length, and pointed to moderately ovoid in shape. The surface of the bud bears between 4 to 9 foliaceous appendages with few stipitate glands and some hairs, usually with slender entire foliaceous parts extending beyond the tip of the bud about ½ or more of its length. Bud color is between 137C and 144A sometimes moderately suffused, especially on the side exposed to the sun, with between 187A and 187B.

The five sepals are about 2.1 to about 4.1 cm. in length and about 0.6 to about 1.2 cm. in width at the widest point. The outer surface color of the sepal is between 137C and 144A sometimes moderately suffused, especially on the side exposed to the sun, with between 187A and 187B. The outer surface of the sepal is somewhat rough and bears between 0 to 3 foliaceous appendages with very few stipitate glands and some hairs. The inner surface color of the sepal is near 146B broadly bordered by near 137B. After the sepals open, the inner surface color is often heavily suffused, especially on the area exposed to the sun, with between 187A and 187B. The inner surface of the sepal is covered with fine wooly tomentum; sepal margins are lined with few stipitate glands and numerous hairs.

The receptacle of the flower is of moderately long length (about 0.5 to about 1.0 cm.) and average to somewhat heavy in caliper (about 0.7 to about 1.2 cm. in diameter). The receptacle is urn-shaped in form. Its surface is smooth with very few hairs and with somewhat thick fleshy walls. The receptacle color is between 146C and 144A sometimes moderately suffused, especially on the side exposed to the sun, with near 183B.

As the petals open (after the calyx breaks), the bud is about 1.8 to about 2.3 cm. in diameter at the widest point, about 2.4 to about 3.0 cm. in length, and moderately ovoid to somewhat pointed in form. The color of the under surfaces of the newly opened petals is between 53A and 59B sometimes moderately suffused on the outermost petals with between 187A and 187B. At the point where the petal attaches, there is a moderately large zone of between 145B and 149C. The color of the upper surfaces of the newly opened petals is between 60A and 59B. At the point where the petal attaches, there is a moderately large zone of between 150C and 154C.

BLOOM

When fully open, the bloom ranges from about 7.9 to about 11.5 cm. in diameter. Petalage is very double with about 30 to 55 petals and about 3 to 15 petaloids irregularly arranged. When partially open, the bloom form is globular to somewhat high centered to cupped, and the petals are loosely spiraled to moderately cupped to somewhat undulated with petal edges somewhat reflexed outward. When fully open, the bloom form is more cupped, and the petals are loosely cupped to somewhat undulated with petal edges somewhat reflexed outward.

PETALS

The substance of the petals is somewhat heavy and of moderately thin thickness, with upper surfaces moderately satiny and under surfaces shiny. The petals are about 3.1 to about 6.3 cm. in length and about 2.5 to about 6.0 cm. in width at the widest point. Petal margins are entire.

The outer petals are broadly obovate to somewhat rounded in shape with rounded to sometimes mucronate apices.

The inner petals are broadly obovate in shape with rounded to sometimes mucronate apices.

Petaloids are about 0.9 to about 4.2 cm. in length and about 0.3 to about 2.6 cm. in width at the widest point. Petaloids are irregularly shaped moderately oblanceolate to somewhat subulate with rounded apices.

NEWLY OPENED FLOWER

The under surface color of the outer and intermediate petals is between 67A and 64C sometimes moderately suffused especially on the outermost petals with between 61A and 61B. At the point where the petal attaches, there is a moderately large zone of between 2D and 150D. The upper surface color of the outer and intermediate petals is between 67A and 64C sometimes moderately suffused especially the outermost petals with between 61A and 61B. At the point where the petal attaches, there is a moderately large zone of between 154D and 1D.

The under surface color of the inner petals is between 67A and 64C. The upper surface color of the inner petals is between 61B and 64C.

The under and upper surface colors of the petaloids are similar in coloration to the upper and under surfaces of the intermediate and inner petals.

The general tonality of the newly opened flower is between 67A and 64C.

THREE-DAY-OLD FLOWER

The under surface color of the outer, intermediate and inner petals is between 64C and 68A sometimes moderately suffused especially on the outermost petals with near 67A. At the point where the petal attaches, there is a moderately large zone of near 150D. The upper surface color of the outer, intermediate and inner petals is between 67A and 68A. At the point where the petal attaches, there is a moderately large zone of between 2D and 150D.

The under and upper surface colors of the petaloids are similar in coloration to the upper and under surfaces of the intermediate and inner petals.

The general tonality of the three-day-old flower is between 67A and 68A.

On the spent bloom, the petals usually drop off cleanly.

In November in Pomona, Calif., blooms on the bush growing outdoors generally last about four to five days. Cut roses from plants grown outdoors and kept at normal indoor living temperatures generally last about four to five days.

MALE REPRODUCTIVE ORGANS

Stamens are many in number (average about 245) and are arranged regularly about the pistils; a few are mixed with petaloids or tucked in the calyx. The filaments are of medium to moderately long length (about 0.5 to about 1.2 cm.) most with anthers. Filaments are between 10A and 11A in color often moderately suffused with near 53C. The anthers are medium to somewhat large for the class and all open approximately at the same time. Anther color when immature is near 22A on the external part and near 11C on the internal part. Anther color at maturity is near 164C on the external part and near 200A on the internal part. Pollen is abundant and between 21A and 23B in color.

FEMALE REPRODUCTIVE ORGANS

Pistils vary in number (average about 100). The styles are moderately uneven, somewhat short to average in length (about 0.3 to about 0.6 cm.), average in caliper, and loosely bunched to somewhat separated. Stigma color is between 14C and 16C. Style color is between 2D and 4D often heavily suffused with between 53A and 53B. Ovaries are usually all enclosed in the calyx. The ovaries are somewhat large and between 158C and 158D in color.

Hips are of moderately long length (about 2.0 to about 3.7 cm.), globular with a flat top in form, and near 31A in color when ripe. The hip surface is smooth with thick fleshy walls. The sepals are fugacious, and usually straight in shape.

The seeds are irregularly rounded, smooth in texture, approximately 10 to about 15 per hip, about 0.3 to about 0.7 cm. in diameter at the widest point and between 165C and 164B in color.

FOLIAGE

The compound leaves are usually comprised of three to seven leaflets and are borne abundantly. The five-leaflets are about 8.2 to about 15.2 cm. in length and about 5.8 to about 12.2 cm. in width at the widest point, moderately leathery to somewhat crisp in texture on both sides, and glossy in finish on the upper side and slightly shiny in finish on the under side. The leaves have a pinnate venation pattern. The terminal leaflets are about 4.2 to about 7.8 cm. in length and about 2.5 to about 4.8 cm. in width at the widest point, shaped ovate with acute apices and rounded bases. Their margins are usually simply serrate.

The upper surface color of the mature leaf is between 137A and 147A. The under surface color of the mature leaf is between 146B and 147B. The under and upper colors of the leaf veins on the mature leaf are similar in coloration to the upper and under surfaces colors of the mature leaf. The upper surface color of the young leaf is between 137A and 146A, sometimes moderately suffused with between 187A and 187B. The under surface color of the young leaf is between 146A and 146B, sometimes moderately suffused with between 187B and 187A. The under and upper colors of the leaf veins on the young leaf are similar in coloration to the upper and under surfaces colors of the young leaf.

The rachis is somewhat light to average in caliper and rough. The upper side is shallowly grooved with very few hairs and stipitate glands on the edges of the grooves. The under side of the rachis is rough with very few stipitate glands and few small prickles. The rachis color is near 146D on the under side and near 144A on the upper side, sometimes moderately suffused on the young leaves with near 187B.

The stipules are about 1.1 to about 2.1 cm. in length and moderately wide (about 0.7 to about 1.0 cm.) with somewhat long straight points that usually turn out at an angle of more than 45 degrees and sometimes recurve toward the stem. The under and upper surface color of the stipule is between 137A and 137B. The upper and under surfaces of the stipules are smooth in texture.

The petiole is somewhat light to average in caliper and rough. The upper side is shallowly grooved with very few hairs and stipitate glands on the edges of the grooves. The under side of the petiole is rough with very few stipitate glands and few small prickles. The petiole is about 0.7 to about 1.8 cm. in length and about 0.1 to about 0.2 cm in width at the widest point. The petiole color is near 146D on the under side and near 144A on the upper side, sometimes moderately suffused on the young leaves with near 187B.

The plant displays an above average degree of resistance to powdery mildew (*Sphaerotheca pannosa*), downy mildew (*Peronospora sparsa*) and rust (*Phragmidium* sp.) as compared to other commercial varieties grown under comparable conditions in Pomona, Calif. The plant is cold hardy to zone 5 and heat tolerant to zone 10.

GROWTH

The plant has an upright somewhat spreading medium height to somewhat tall growing habit (about 145 to about 180 cm. in height and about 110 to about 135 cm. spread at the widest point), with full branching. It displays moderately vigorous growth and the canes are of medium size caliper for the class (about 1.6 to about 2.3 cm. in diameter at the widest point).

The color of the major stems is between 147B and 146B. The major stems are rough in texture and they bear many large prickles that are about 0.7 to about 1.2 cm. in length. The large prickles are angled slightly downward with a moderately short broad oval base; prickle color is near 199A often moderately suffused with between 201B and 201C. The major stem bears some small prickles of similar shape and coloration.

The color of the branches is between 146B and 146A. The branches are rough in texture and they bear many large prickles which are of similar size and shape to the large prickles on the major stems; prickle color is between 161C and 162D sometimes lightly suffused with near 187D. The branches bear few small prickles of similar shape and coloration.

The color of the new shoots is between 146B and 143A sometimes lightly suffused with between 187B and 187C. The new shoots are rough in texture and they bear many large prickles which are of similar size and shape to the large prickles on the major stems; prickle color is between 145A and 146D sometimes lightly suffused with between 187B and 187C. The shoots bear few small prickles of similar shape and coloration.

I claim:

1. A new and distinct Hybrid Tea rose plant of the variety substantially as described and illustrated herein.

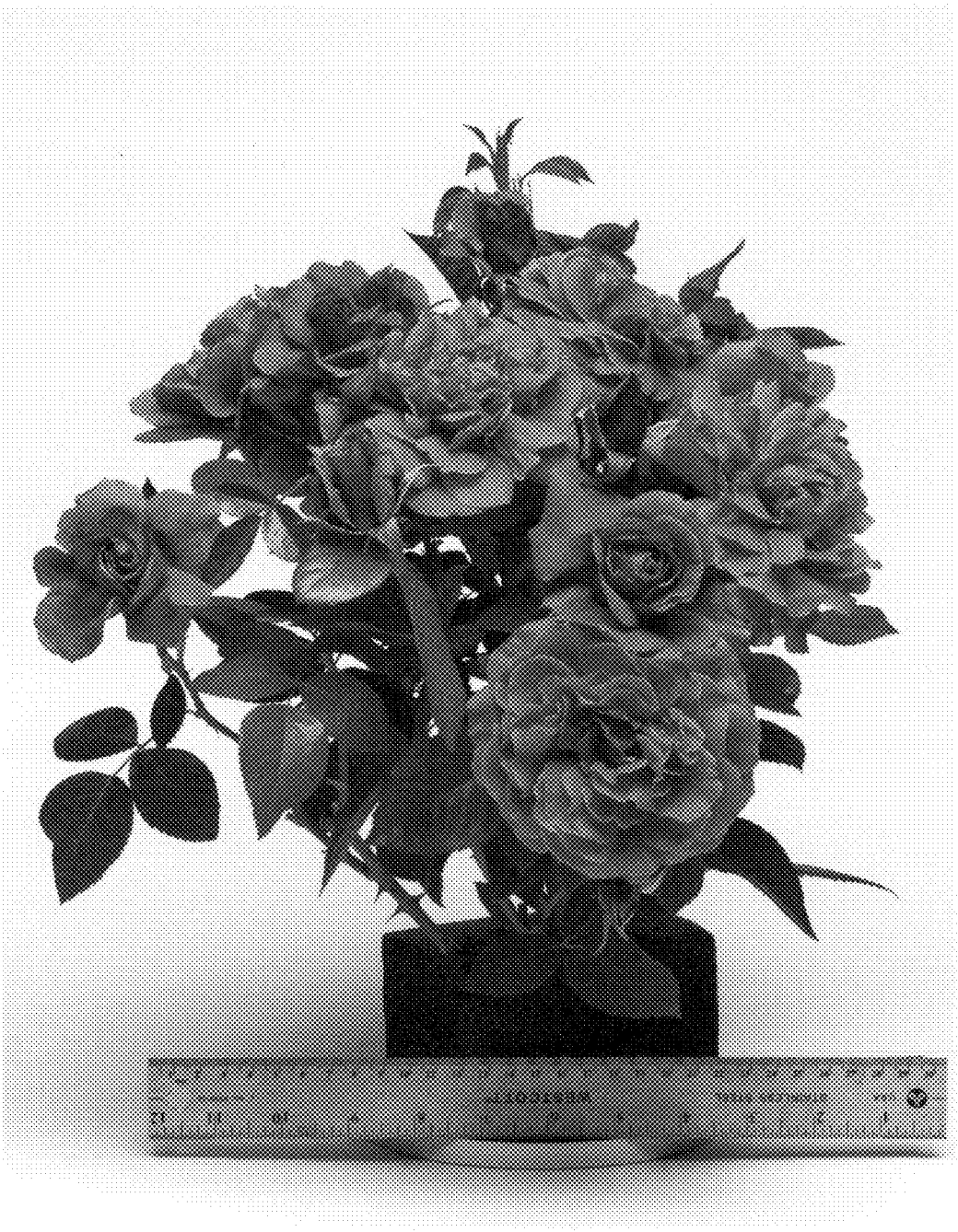

* * * * *